US012811006B2

(12) United States Patent
Weydt et al.

(10) Patent No.: US 12,811,006 B2
(45) **Date of Patent: *Nov. 24, 2026**

(54) ADJUSTING DIABETES ALERTS AND THERAPY BASED ON GESTURE-BASED DETECTION OF VEHICLE OPERATION

(71) Applicant: Medtronic MiniMed, Inc., Northridge, CA (US)

(72) Inventors: Patrick E. Weydt, Moorpark, CA (US); Pratik J. Agrawal, Stevenson Ranch, CA (US); Louis J. Lintereur, Boise, ID (US); Lavie Golenberg, Singaore (SG); David Dunleavy, West Hills, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/633,388

(22) Filed: Apr. 11, 2024

(65) Prior Publication Data

US 2024/0257965 A1 Aug. 1, 2024

Related U.S. Application Data

(63) Continuation of application No. 17/004,981, filed on Aug. 27, 2020, now Pat. No. 11,990,236.

(Continued)

(51) Int. Cl.
*G16H 40/63* (2018.01)
*A61B 5/00* (2006.01)

(Continued)

(52) U.S. Cl.
CPC ............. *G16H 40/63* (2018.01); *A61B 5/746* (2013.01); *G06F 3/017* (2013.01); *G16H 20/17* (2018.01);

(Continued)

(58) Field of Classification Search
CPC ....... H04M 1/72454; H04M 1/72463–724634; G06F 3/017
See application file for complete search history.

(56) References Cited

U.S. PATENT DOCUMENTS

| | | | |
|---|---|---|---|
| 7,935,076 | B2 | 5/2011 | Estes et al. |
| 9,008,803 | B2 | 4/2015 | Blomquist |

(Continued)

FOREIGN PATENT DOCUMENTS

| | | | |
|---|---|---|---|
| CN | 109789264 | A | 5/2019 |
| EP | 3417773 | A1 | 12/2018 |

(Continued)

OTHER PUBLICATIONS

Castle, J.R., et al., "Future of Automated Insulin Delivery Systems," Diabetes Technology Therapeutics, Jun. 2017, vol. 19(S3), pp. S67-S72.

(Continued)

*Primary Examiner* — Karen A Hranek
(74) *Attorney, Agent, or Firm* — Weaver Austin Villeneuve & Sampson LLP

(57) ABSTRACT

Disclosed herein are techniques for delivery of diabetes therapy. In some embodiments, the techniques may involve receiving, using one or more processors of an insulin pump, gesture data indicative of a gesture of a patient using the insulin pump. The techniques may further involve determining, by the one or more processors of the insulin pump and based on a connection to a short-range communication system of a vehicle, that the patient is in the vehicle and determining, based at least in part on the gesture data, that the patient is operating the vehicle. The techniques may further involve determining, using the one or more processors of the insulin pump, a driving therapy protocol based on the determination that the patient is operating the vehicle.

19 Claims, 8 Drawing Sheets

Related U.S. Application Data

(60) Provisional application No. 62/893,717, filed on Aug. 29, 2019, provisional application No. 62/893,722, filed on Aug. 29, 2019.

(51) Int. Cl.

| | |
|---|---|
| ***G06F 3/01*** | (2006.01) |
| ***G16H 20/17*** | (2018.01) |
| ***H04M 1/72454*** | (2021.01) |
| ***H04M 1/72463*** | (2021.01) |

(52) U.S. Cl.
CPC .... *H04M 1/72454* (2021.01); *H04M 1/72463* (2021.01)

(56) References Cited

U.S. PATENT DOCUMENTS

| | | | | |
|---|---|---|---|---|
| 9,037,125 | B1 * | 5/2015 | Kadous | H04W 4/027 455/418 |
| 9,672,328 | B2 | 6/2017 | Saint et al. | |
| 9,971,874 | B2 | 5/2018 | Jafari et al. | |
| 10,080,840 | B2 | 9/2018 | Gescheit et al. | |
| 10,214,221 | B2 * | 2/2019 | Chen | G06F 1/163 |
| 10,258,745 | B2 | 4/2019 | Despa et al. | |
| 10,307,538 | B2 | 6/2019 | Desborough et al. | |
| 11,551,812 | B2 | 1/2023 | Weydt et al. | |
| 11,710,562 | B2 | 7/2023 | Weydt et al. | |
| 11,990,236 | B2 | 5/2024 | Weydt et al. | |
| 12,354,745 | B2 | 7/2025 | Weydt et al. | |
| 12,478,732 | B2 | 11/2025 | Golenberg et al. | |
| 2012/0289217 | A1 * | 11/2012 | Riemer | H04M 1/67 455/418 |
| 2013/0217990 | A1 | 8/2013 | Saettel et al. | |
| 2013/0245545 | A1 * | 9/2013 | Arnold | A61M 5/1723 604/66 |
| 2013/0316737 | A1 * | 11/2013 | Guba | H04W 4/027 455/456.4 |
| 2014/0012510 | A1 | 1/2014 | Mensinger et al. | |
| 2014/0184772 | A1 | 7/2014 | Hanina et al. | |
| 2014/0315162 | A1 | 10/2014 | Ehrenkranz | |
| 2015/0246179 | A1 | 9/2015 | Zur et al. | |
| 2016/0306932 | A1 | 10/2016 | Fateh et al. | |
| 2017/0053552 | A1 | 2/2017 | Zhong et al. | |
| 2017/0150360 | A1 | 5/2017 | Caldwell et al. | |
| 2017/0189625 | A1 | 7/2017 | Cirillo et al. | |
| 2017/0203030 | A1 | 7/2017 | Brewer et al. | |
| 2017/0203039 | A1 * | 7/2017 | Desborough | G16H 40/60 |
| 2017/0228518 | A1 | 8/2017 | Booth et al. | |
| 2017/0249445 | A1 | 8/2017 | DeVries et al. | |
| 2017/0257844 | A1 | 9/2017 | Miller et al. | |
| 2017/0311903 | A1 | 11/2017 | Davis et al. | |
| 2017/0332347 | A1 | 11/2017 | Boss et al. | |
| 2018/0104412 | A1 * | 4/2018 | Henrich | A61M 5/14244 |
| 2018/0109412 | A1 | 4/2018 | Xuan et al. | |
| 2018/0147362 | A1 | 5/2018 | Arenas Latorre et al. | |
| 2018/0199890 | A1 * | 7/2018 | Hayter | A61B 5/4866 |
| 2018/0214077 | A1 | 8/2018 | Dunki-Jacobs et al. | |
| 2018/0271418 | A1 | 9/2018 | Hayter et al. | |
| 2019/0052748 | A1 * | 2/2019 | Stewart | H04M 1/72463 |
| 2019/0158447 | A1 | 5/2019 | Aggarwal et al. | |
| 2019/0182749 | A1 | 6/2019 | Breaux et al. | |
| 2019/0236465 | A1 * | 8/2019 | Vleugels | G16H 10/60 |
| 2019/0246914 | A1 | 8/2019 | Constantin et al. | |
| 2019/0246973 | A1 | 8/2019 | Constantin et al. | |
| 2019/0252079 | A1 | 8/2019 | Constantin et al. | |
| 2019/0274624 | A1 | 9/2019 | Mazlish et al. | |
| 2019/0382025 | A1 | 12/2019 | Mena Benito et al. | |
| 2020/0016338 | A1 * | 1/2020 | Sloan | G16H 50/50 |
| 2020/0129099 | A1 | 4/2020 | Mi et al. | |
| 2020/0152312 | A1 | 5/2020 | Connor | |
| 2021/0060247 | A1 | 3/2021 | Weydt et al. | |
| 2021/0065894 | A1 | 3/2021 | Weydt et al. | |
| 2021/0256872 | A1 * | 8/2021 | Matsumoto | G16H 50/20 |
| 2023/0121873 | A1 | 4/2023 | Weydt et al. | |
| 2023/0317277 | A1 | 10/2023 | Weydt et al. | |
| 2025/0299817 | A1 | 9/2025 | Weydt et al. | |

FOREIGN PATENT DOCUMENTS

| | | | |
|---|---|---|---|
| KR | 20180028823 | A | 3/2018 |
| WO | 2014115025 | A1 | 7/2014 |
| WO | 2017027258 | A1 | 2/2017 |

OTHER PUBLICATIONS

Communication pursuant to Rules 161(1) and 162 EPC from counterpart European Application No. 20771398.3 dated Apr. 5, 2022, 3 pages.
Gomez-Peralta, F., et al., "A Novel Insulin Delivery Optimization and Tracking System," Diabetes Technology Therapeutics, Apr. 2019, vol. 21(4), pp. 209-214.
International Preliminary Report on Patentability dated Mar. 10, 2022 in PCT Application No. PCT/US2020/048446.
International Preliminary Report on Patentability dated Mar. 10, 2022 in PCT Application No. PCT/US2020/048461.
International Search Report and Written Opinion dated Nov. 6, 2020 in PCT Application No. PCT/US2020/048461.
International Search Report and Written Opinion dated Nov. 20, 2020 in PCT Application No. PCT/US2020/048446.
Notice of Allowance from U.S. Appl. No. 17/004,951 dated Sep. 15, 2022, 8 pages.
Response to Communication pursuant to Rules 161(1) and 162 EPC dated Apr. 5, 2022, from counterpart European Application No. 20771398.3, filed Aug. 10, 2022, 15 pages.
Shivers J., et al., "Turn It Off: Diabetes Device Alarm Fatigue Considerations for the Present and the Future," Journal of Diabetes Science and Technology, May 2013, vol. 7 (3), pp. 789-794.
U.S. Advisory Action dated Dec. 13, 2023 in U.S. Appl. No. 17/004,981.
U.S. Final Office Action dated Oct. 27, 2023 in U.S. Appl. No. 17/004,981.
U.S. Non-Final Office Action dated Jul. 6, 2023, in U.S. Appl. No. 17/004,981.
U.S. Notice of Allowance dated Jan. 23, 2024 in U.S. Appl. No. 17/004,981.
U.S. Office Action dated Sep. 15, 2022, in U.S. Appl. No. 17/004,951.
U.S. Appl. No. 18/331,515, inventors Weydt et al., filed Jun. 8, 2023.
CN Office Action dated Nov. 29, 2024 in CN Application No. 202080059875.2, with English translation.
EP Office Action dated Aug. 9, 2024, in EP Application No. 20771398.3.
U.S. Non-Final Office Action dated Nov. 25, 2024 in U.S. Appl. No. 18/067,417.
U.S. Notice of Allowance dated Mar. 12, 2025 in U.S. Appl. No. 18/067,417.
CA Office Action dated Oct. 6, 2025 in CA Application No. 3150589.
CA Office Action dated Oct. 8, 2025 in CA Application No. 3150586.
CA Office Action dated Jun. 11, 2026 in CA Application No. 3,150,589.
U.S. Notice of Allowance dated May 19, 2026 in U.S. Appl. No. 18/331,515.
U.S. Non-Final Office Action dated Feb. 6, 2026 in U.S. Appl. No. 18/331,515.

* cited by examiner

ADJUSTING DIABETES ALERTS AND THERAPY BASED ON GESTURE-BASED DETECTION OF VEHICLE OPERATION

This application is a continuation of U.S. patent application Ser. No. 17/004,981, filed on Aug. 27, 2020, titled "ADJUSTING DIABETES ALERTS AND THERAPY BASED ON GESTURE-BASED DETECTION OF VEHICLE OPERATION," which claims the benefit of U.S. Provisional Application No. 62/893,717, titled "INCORPORATING GESTURE DETECTION AND BIOSENSORS INTO DIABETES THERAPIES," filed Aug. 29, 2019, and U.S. Provisional Application No. 62/893,722, titled "INCORPORATING GESTURE DETECTION AND BIOSENSORS INTO DIABETES THERAPIES," filed Aug. 29, 2019, the entire content of each of which is incorporated by reference herein.

TECHNICAL FIELD

The disclosure relates to medical systems and, more particularly, to medical systems for therapy for diabetes.

BACKGROUND

A patient with diabetes receives insulin from a pump or injection device to control the glucose level in his or her bloodstream. Naturally produced insulin may not control the glucose level in the bloodstream of a diabetes patient due to insufficient production of insulin and/or due to insulin resistance. To control the glucose level, a patient's therapy routine may include dosages of basal insulin and bolus insulin. Basal insulin, also called background insulin, tends to keep blood glucose levels at consistent levels during periods of fasting and is a long acting or intermediate acting insulin. Bolus insulin may be taken specifically at or near mealtimes or other times where there may be a relatively fast change in glucose level, and may therefore serve as a short acting or rapid acting form of insulin dosage.

SUMMARY

Disclosed herein are techniques for delivery of diabetes therapy. The techniques may be practiced with a processor-implemented method, a system comprising one or more processors and one or more processor-readable media, and/or one or more non-transitory processor readable media.

In some embodiments, the techniques may involve receiving, using one or more processors of an insulin pump, gesture data indicative of a gesture of a patient using the insulin pump. The techniques may further involve determining, by the one or more processors of the insulin pump and based on a connection to a short-range communication system of a vehicle, that the patient is in the vehicle and determining, based at least in part on the gesture data, that the patient is operating the vehicle. The techniques may further involve determining, using the one or more processors of the insulin pump, a driving therapy protocol based on the determination that the patient is operating the vehicle.

The details of one or more aspects of the disclosure are set forth in the accompanying drawings and the description below. Other features, objects, and advantages of this disclosure will be apparent from the description and drawings, and from the claims.

DETAILED DESCRIPTION

Figure 1:
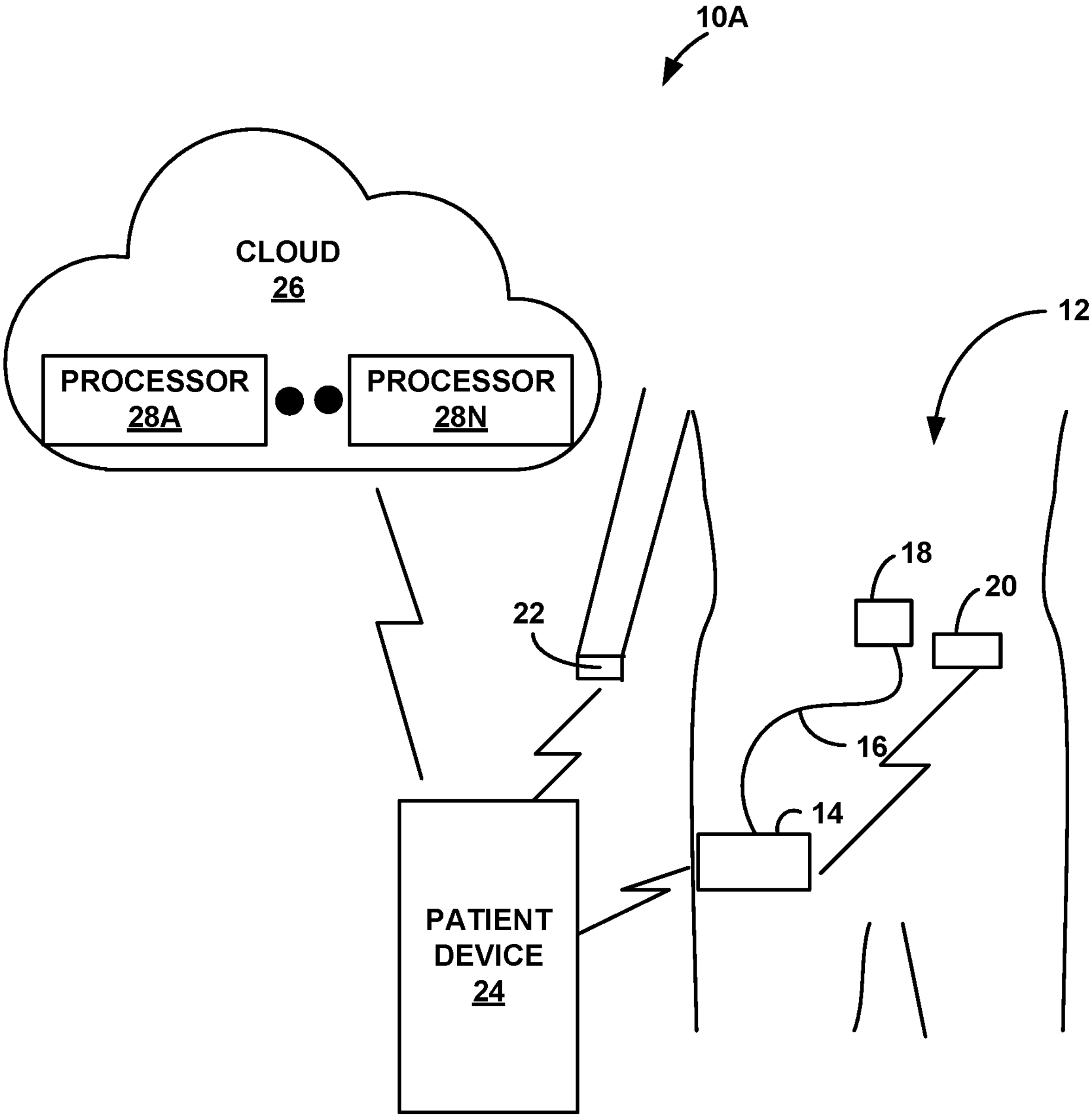
FIG. 1 is a block diagram illustrating an example system for delivering or guiding therapy dosage, in accordance with one or more examples described in this disclosure.

Devices, systems, and techniques for managing alerts related to diabetes treatment and for managing glucose level in a patient are described in this disclosure. Diabetic therapy often includes the injection of insulin into a patient in order to maintain a target blood glucose level. The insulin may be injected manually by the patient or automatically injected using an insulin pump. In many circumstances, the patient will carry a patient device (e.g., smartphone, tablet, etc.) that provides the patient notifications and alerts concerning their diabetes therapy, as well as interfaces for controlling the operation of the insulin pump. In some situations, such as operating a vehicle, it may be desirable to reduce driver distractions and/or reduce the possibility of a hypoglycemic (e.g., low blood glucose) event. A hypoglycemic event may impair the patient's ability to concentrate and/or make quick physical movements, thus impacting the operation of a motor vehicle.

In accordance with the techniques of this disclosure, one or more systems or devices may automatically detect whether a patient is operating a vehicle. As will be described below, detection of the operation of a vehicle may be based on the automatic detection of one or more gestures of a patient. By using gesture detection, rather than merely the position and/or speed of the patient, the techniques of this disclosure may allow for discerning that the patient is operating the vehicle, rather than merely being a passenger.

When detected that the patient is operating the vehicle, the techniques of this disclosure further include one or more of altering the alerts that are output by a patient device and/or altering the therapy provided by an insulin pump. In one example, when it is detected that a patient is operating a vehicle, the patient device may be configured to output fewer alerts, so as to reduce distractions to the driver. Higher priority alerts (e.g., low blood glucose alert) may still be output, while lower priority alerts (e.g., low battery, meal reminders, etc.) may be disabled and/or reduced in frequency relative to a default alert protocol.

For example, lower priority alerts may be completely disabled while driving. In another example, lower priority alerts may be held (e.g., not output) until the system detects the patient is no longer driving and then the low priority alerts may be output at that time. In another example, the lower priority alerts may still be output while the patient is driving, but may be output less frequently relative to a default alert protocol. In another example, lower priority alerts may be output to a display, but sound and/or haptics related with such lower priority alerts may be disabled.

In some examples, when it is detected that a patient is operating a vehicle, the insulin pump may be configured to operate according to a higher target blood glucose level with or without patient confirmation and/or configured to reduce the insulin dosage with or without patient confirmation so as to reduce the likelihood of a hypoglycemic event. As such, the gesture-based techniques for the automatic detection of vehicle operation may enhance the safety of vehicle operation of a diabetic patient, without unnecessarily maintaining a higher blood glucose level in the patient when the patient is merely a passenger in a vehicle.

FIG. 1 is a block diagram illustrating an example system for outputting user alerts and/or delivering or guiding diabetes therapy in accordance with one or more examples described in this disclosure. FIG. 1 illustrates system 10A that includes patient 12, insulin pump 14, tubing 16, infusion set 18, sensor 20, which may be a glucose sensor, wearable device 22, patient device 24, and cloud 26. Cloud 26 represents a local, wide area or global computing network including one or more processors 28A-28N ("one or more processors 28"). In some examples, the various components may determine changes to therapy based on a determination of a glucose level from sensor 20, and therefore system 10A may be referred to as a continuous glucose monitoring (CGM) system 10A.

Patient 12 may be diabetic patient (e.g., Type 1 diabetic or Type 2 diabetic patient), and therefore, the glucose level in patient 12 may be uncontrolled without delivery of supplemental insulin. For example, patient 12 may not produce sufficient insulin to control the glucose level or the amount of insulin that patient 12 produces may not be sufficient due to insulin resistance that patient 12 may have developed.

To receive the supplemental insulin, patient 12 may carry insulin pump 14 that couples to tubing 16 for delivery of insulin into patient 12. Infusion set 18 may connect to the skin of patient 12 and include a cannula to deliver insulin into patient 12. Sensor 20 may also be coupled to patient 12 to measure glucose level in patient 12. Insulin pump 14, tubing 16, infusion set 18, and Sensor 20 may together form an insulin pump system. One example of the insulin pump system is the MINIMED™ 670G INSULIN PUMP SYSTEM by Medtronic, Inc. However, other examples of insulin pump systems may be used, and the example techniques should not be considered limited to the MINIMED™ 670G INSULIN PUMP SYSTEM. For example, the techniques described in this disclosure may be utilized in insulin pump systems that include wireless communication capabilities. However, the example techniques should not be considered limited to insulin pump systems with wireless communication capabilities, and other types of communication, such as wired communication, may be possible. In another example, insulin pump 14, tubing 16, infusion set 18, and/or sensor 20 may be contained in the same housing.

Insulin pump 14 may be a relatively small device that patient 12 can place in different locations. For instance, patient 12 may clip insulin pump 14 to the waistband of trousers worn by patient 12. In some examples, to be discreet, patient 12 may place insulin pump 14 in a pocket. In general, insulin pump 14 can be worn in various places and patient 12 may place insulin pump 14 in a location based on the particular clothes patient 12 is wearing.

To deliver insulin, insulin pump 14 includes one or more reservoirs (e.g., two reservoirs). A reservoir may be a plastic cartridge that holds up to N units of insulin (e.g., up to 300 units of insulin) and is locked into insulin pump 14. Insulin pump 14 may be a battery powered device that is powered by replaceable and/or rechargeable batteries.

Tubing 16, sometimes called a catheter, connects on a first end to a reservoir in insulin pump 14 and connects on a second end to infusion set 18. Tubing 16 may carry the insulin from the reservoir of insulin pump 14 to patient 12. Tubing 16 may be flexible, allowing for looping or bends to minimize concern of tubing 16 becoming detached from insulin pump 14 or infusion set 18 or concern from tubing 16 breaking.

Infusion set 18 may include a thin cannula that patient 12 inserts into a layer of fat under the skin (e.g., subcutaneous connection). Infusion set 18 may rest near the stomach of patient 12. The insulin travels from the reservoir of insulin pump 14, through tubing 16, and through the cannula in infusion set 18, and into patient 12. In some examples, patient 12 may 12 may utilize an infusion set insertion device. Patient 12 may place infusion set 18 into the infusion set insertion device, and with a push of a button on the infusion set insertion device, the infusion set insertion device may insert the cannula of infusion set 18 into the layer of fat of patient 12, and infusion set 18 may rest on top of the skin of the patient with the cannula inserted into the layer of fat of patient 12.

Sensor 20 may include a cannula that is inserted under the skin of patient 12, such as near the stomach of patient 12 or in the arm of patient 12 (e.g., subcutaneous connection). The Sensor 20 may be configured to measure the interstitial glucose level, which is the glucose found in the fluid between the cells of patient 12. Sensor 20 may be configured to continuously or periodically sample the glucose level and rate of change of the glucose level over time.

In one or more examples, insulin pump 14 and sensor 20, and the various components illustrated in FIG. 1, may together form a closed-loop therapy delivery system. For example, patient 12 may set a target glucose level, usually measured in units of milligrams per deciliter, on insulin pump 14. Insulin pump 14 may receive the current glucose level from sensor 20, and in response may increase or decrease the amount of insulin delivered to patient 12. For example, if the current glucose level is higher than the target glucose level, insulin pump 14 may 14 may increase the insulin. If the current glucose level is lower than the target glucose level, insulin pump 14 may temporarily cease delivery of the insulin. Insulin pump 14 may be considered as an example of an automated insulin delivery (AID) device. Other examples of AID devices may be possible, and the techniques described in this disclosure may be applicable to other AID devices.

For example, insulin pump 14 and sensor 20 may be configured to operate together to mimic some of the ways in which a healthy pancreas works. Insulin pump 14 may be configured to deliver basal insulin, which is a small amount of insulin released continuously throughout the day. There may be times when glucose levels increase, such as due to eating or some other activity that patient 12 undertakes. Insulin pump 14 may be configured to deliver bolus insulin on demand in association with food intake or to correct an undesirably high glucose level in the bloodstream. In one or more examples, if the glucose level rises above a target level, then insulin pump 14 may increase the bolus insulin to address the increase in glucose level. Insulin pump 14 may be configured to compute basal and bolus insulin delivery, and deliver the basal and bolus insulin accordingly. For instance, insulin pump 14 may determine the amount of basal insulin to deliver continuously, and then determine the amount of bolus insulin to deliver to reduce glucose level in response to an increase in glucose level due to eating or some other event.

Accordingly, in some examples, sensor 20 may sample glucose level and rate of change in glucose level over time. Sensor 20 may output the glucose level to insulin pump 14 (e.g., through a wireless link connection like Bluetooth or BLE). Insulin pump 14 may compare the glucose level to a target glucose level (e.g., as set by patient 12 or clinician), and adjust the insulin dosage based on the comparison. In some examples, sensor 20 may also output a predicted glucose level (e.g., where glucose level is expected to be in the next 30 minutes), and insulin pump 14 may adjust insulin delivery based on the predicted glucose level.

As described above, patient 12 or a clinician may set the target glucose level on insulin pump 14. There may be various ways in which patient 12 or the clinician may set the target glucose level on insulin pump 14. As one example, patient 12 or the clinician may utilize patient device 24 to communicate with insulin pump 14. Examples of patient device 24 include mobile devices, such as smartphones or tablet computers, laptop computers, and the like. In some examples, patient device 24 may be a special programmer or controller for insulin pump 14. Although FIG. 1 illustrates one patient device 24, in some examples, there may be a plurality of patient devices. For instance, system 10A may include a mobile device and a controller, each of which are examples of patient device 24. For ease of description only, the example techniques are described with respect to patient device 24, with the understanding that patient device 24 may 24 may be one or more patient devices.

Patient device 24 may also be configured to interface with sensor 20. As one example, patient device 24 may receive information from sensor 20 through insulin pump 14, where insulin pump 14 relays the information between patient device 24 and sensor 20. As another example, patient device 24 may receive information (e.g., glucose level or rate of change of glucose level) directly from sensor 20 (e.g., through a wireless link).

In one or more examples, patient device 24 may display a user interface with which patient 12 or the clinician may control insulin pump 14. For example, patient device 24 may 24 may display a screen that allows patient 12 or the clinician to enter the target glucose level. As another example, patient device 24 may display a screen that outputs the current and/or past glucose level. In some examples, patient device 24 may output notifications and/or alerts to patient 12, such as alerts if the glucose level is too high or too low, as well as alerts regarding any action that patient 12 needs to take. For example, if the batteries of insulin pump 14 are low on charge, then insulin pump 14 may output a low battery indication to patient device 24, and patient device 24 may in turn output a notification to patient 12 to replace or recharge the batteries.

In some examples, patient device 24 may be configured to categorize alerts as being high priority alerts or low priority alerts. High priority alerts may include alerts that indicate a low or dropping blood glucose level, alerts that indicate a high or spiking blood glucose level, and alerts that instruct patient 12 to take action regarding their therapy (e.g., instructions to manually inject insulin). Other examples of high priority alerts may include sever low blood glucose (e.g., less than 54 mg/dL) and/or alerts for insulin pump 14 that indicate that therapy has stopped, e.g., due to occlusion, dead battery ("replace battery now"), reservoir empty, or critical pumping errors. Low priority alerts may include other, non-safety critical alerts, such as reminders to take medication, reminders to eat, low-battery alerts, change/replace sensor 20, and the like. As will be explained in more detail below, based on a detection that patient 12 is operating a vehicle, patient device 24 may be configured to reduce the output frequency (e.g., relative to some default frequency) and/or disable low priority alerts during the time that patient 12 is operating the vehicle. In this scenario, patient device 24 may continue to output high priority alerts at the default frequency.

In some examples, patient device 24 may completely disable lower priority alerts when it is detected that patient 12 is driving. In another example, patient device 24 may hold lower priority alerts (e.g., not output) until patient device 24 and/or processors 28 detect that patient 12 is no longer driving and then patient device 24 may output the low priority alerts at that time. In another example, patient device 24 may still output the lower priority alerts while patient 12 is driving, but may be output the lower priority alerts less frequently relative to a default alert protocol. In another example, patient device 24 may output lower priority alerts to a display of patient device 24, but patient device 24 may disable sound and/or haptics related with such lower priority alerts.

Techniques of this disclosure are described with relation to patient device 24 outputting one or more alerts and adjusting how such alerts are output when it is detected that patient 12 is driving a vehicle. However, the techniques of this disclosure apply equally to any alerts output or generated by any of insulin pump 14, patient device 24, and/or wearable device 22. For example, insulin pump 14 may generate alerts to be output by patient device 24 and/or wearable device 22. The techniques of this disclosure may cause insulin pump to refrain from generating and/or transmitting lower priority alerts in the situation where it is detected that patient 12 is driving.

In some examples of the disclosure, based on a detection of patient 12 operating a vehicle, patient device 24 may be configured to alter the therapy provided by insulin pump 14. In order to avoid unwanted hypoglycemic events while operating a vehicle, patient device 24 may send instructions to insulin pump 14 to raise a target glucose level and/or reduce the dosage of insulin given to patient 12.

Controlling insulin pump 14 through patient device 24 is one example, and should not be considered limiting. For example, insulin pump 14 may include a user interface (e.g., pushbuttons) that allow patient 12 or the clinician to set the various glucose levels of insulin pump 14. Also, in some examples, insulin pump 14 itself, or in addition to patient device 24, may be configured to output notifications to patient 12. In some examples, insulin pump 14 may 14 may generate and/or transmit alerts to patient device 24 and/or wearable device 22 for output by patient device 24 and/or wearable device 22. For instance, if the glucose level is too high or too low, insulin pump 14 may output an audible or haptic output. As another example, if the battery is low, then insulin pump 14 may output a low battery indication on a display of insulin pump 14.

The above describes examples ways in which insulin pump 14 may deliver insulin to patient 12 based on the current glucose levels (e.g., as measured by sensor 20). In some cases, there may be therapeutic gains by proactively delivering insulin to patient 12, rather than reacting to when glucose levels become too high or too low.

The glucose level in patient 12 may increase due to particular user actions. As one example, the glucose level in patient 12 may increase due to patient 12 engaging in an activity like eating or exercising. In some examples, there may be therapeutic gains if it is possible to determine that patient 12 is engaging in the activity, and delivering insulin based on the determination that patient 12 is engaging in the activity.

For example, patient 12 may forget to cause insulin pump 14 to deliver insulin after eating, resulting an insulin shortfall. Alternatively, patient 12 may cause insulin pump 14 to deliver insulin after eating but may have forgotten that patient 12 previously caused insulin pump 14 to deliver insulin for the same meal event, resulting in an excessive insulin dosage. Also, in examples where sensor 20 is utilized, insulin pump 14 may not take any action until after the glucose level is greater than a target level. By proactively determining that patient 12 is engaging in an activity, insulin pump 14 may be able to deliver insulin in such a manner that the glucose level does not rise above the target level or rises only slightly above the target level (i.e., rises by less than what the glucose level would have risen if insulin were not delivered proactively). In some cases, by proactively determining that patient 12 is engaging in an activity and delivering insulin accordingly, the glucose level of patient 12 may increase more slowly.

Although the above describes proactive determination of patient 12 eating and delivering insulin accordingly, the example techniques are not so limited. The example techniques may be utilized for proactively determining an activity that patient 12 is undertaking (e.g., eating, exercising, sleeping, driving, etc.). Insulin pump 14 may then deliver insulin based on the determination of the type of activity patient 12 is undertaking.

For example, processors 28 of cloud 26 (described in more detail below), patient device 24, wearable device 22, and/or insulin pump 14 may be configured to determine that patient 12 is operating a vehicle. Based on such a determination, processors 28 of cloud 26, patient device 24, wearable device 22, and/or insulin pump 14 may instruct insulin pump 14 to deliver a driving therapy protocol to patient 12. The driving therapy protocol may be configured to maintain a higher blood glucose level and/or reduce the possibility of a hypoglycemic event in patient 12 during the time in which patient 12 is operating the vehicle. In one example, relative to a default therapy protocol, insulin pump 14 may operate according to a higher target blood glucose level when operating according to the driving therapy protocol. In another example, relative to a default therapy protocol, insulin pump 14 may be configured to deliver a lower dosage of insulin when operating according to the driving therapy protocol. In another example, relative to a default therapy protocol, insulin pump 14 may operate according to a higher target blood glucose level and deliver a lower dosage of insulin when operating according to the driving therapy protocol.

As illustrated in FIG. 1, patient 12 may wear wearable device 22. Examples of wearable device 22 include a smartwatch or a fitness tracker, either of which may in some examples, be configured to be worn on a patient's wrist or arm. In one or more examples, wearable device 22 includes an inertial measurement unit, such as a six-axis inertial measurement unit. The six-axis inertial measurement unit may couple a 3-axis accelerometer with a 3-axis gyroscope. Accelerometers measure linear acceleration, while gyroscopes measure rotational motion. Wearable device 22 may be configured to determine one or more movement characteristics of patient 12. Examples of the one or more movement characteristics include values relating to frequency, amplitude, trajectory, position, velocity, acceleration and/or pattern of movement instantaneously or over time. The frequency of movement of the patient's arm may refer to how many times patient 12 repeated a movement within a certain time (e.g., such as frequency of movement back and forth between two positions).

Patient 12 may wear wearable device 22 on his or her wrist. However, the example techniques are not so limited. Patient 12 may wear wearable device 22 on a finger, forearm, or bicep. In general, patient 12 may wear wearable device 22 anywhere that can be used to determine gestures indicative of eating, such as movement characteristics of the arm.

The manner in which patient 12 is moving his or her arm (i.e., the movement characteristics) may refer to the direction, angle, and orientation of the movement of the arm of patient 12, including values relating to frequency, amplitude, trajectory, position, velocity, acceleration and/or pattern of movement instantaneously or over time. As an example, if patient 12 is eating, then the arm of patient 12 will be oriented in a particular way (e.g., thumb is facing towards the body of patient 12), the angle of movement of the arm will be approximately a 90-degree movement (e.g., starting from plate to mouth), and the direction of movement of the arm will be a path that follows from plate to mouth. The forward/backward, up/down, pitch, roll, yaw measurements from wearable device 22 may be indicative of the manner in which patient 12 is moving his or her arm. Also, patient 12 may have a certain frequency at which patient 12 moves his or her arm or a pattern at which patient 12 moves his or her arm that is more indicative of eating, as compared to other activities, like smoking or vaping, where patient 12 may raise his or her arm to his or her mouth.

Although the above description describes wearable device 22 as being utilized to determine whether patient 12 is eating, wearable device 22 may be configured to detect movements of the arm of patient 12 (e.g., one or more movement characteristics), and the movement characteristics may be utilized to determine an activity undertaken by patient 12. For instance, the movement characteristics detected by wearable device 22 may indicate whether patient 12 is exercising, driving, sleeping, etc. As another example, wearable device 22 may 22 may indicate posture of patient 12, which may align with a posture for exercising, driving, sleeping, eating, etc. Another term for movement characteristics may be gesture movements. Accordingly, wearable device 22 may be configured to detect gesture movements (i.e., movement characteristics of the arm of patient 12) and/or posture, where the gesture and/or posture may be part of various activities (e.g., eating, exercising, driving, sleeping, etc.).

In some examples, wearable device 22 may be configured to determine, based on the detected gestures (e.g., movement characteristics of the arm of patient 12) and/or posture, the particular activity patient 12 is undertaking. For example, wearable device 22 may be configured to determine whether patient 12 is eating, exercising, driving, sleeping, etc. In some examples, wearable device 22 may output information indicative of the movement characteristics of the arm of patient 12 and/or posture of patient 12 to patient device 24, and patient device 24 may be configured to determine the activity patient 12 is undertaking.

Gestures that may be indicative of driving may include gestures related to interacting with vehicle controls, including forearm rotation (e.g., both pronation and supination for light steering of the wheel), hand-over-hand motions (e.g., for larger turns of the wheel), grasping (e.g., to hold the steering wheel), up and down motions of the left hand (e.g., to activate turn signals), and back-and-forth motions of the right hand (e.g., shifting the transmission). Wearable device 22 may be configured to detect other gestures that are indicative of operating a vehicle. In addition, as mentioned above, wearable device 22 may also detect certain static postures that are indicative of driving. Such static postures may include both hands held out away from the chest (e.g., when both hands are on the steering wheel) and/or one handheld out away from the chest with another hand in the patient's lap (e.g., one hand on the steering wheel).

Wearable device 22 and/or patient device 24 may be programmed with information that wearable device 22 and/or patient device 24 utilize to determine the particular activity patient 12 is undertaking. For example, patient 12 may undertake various activities throughout the day where the movement characteristics of the arm of patient 12 may be similar to the movement characteristics of the arm of patient 12 for a particular activity, but patient 12 is not undertaking that activity. As one example, patient 12 yawning and cupping his or her mouth may have a similar movement as patient 12 eating. Patient 12 picking up groceries may have similar movement as patient 12 exercising. Also, in some examples, patient 12 may be undertaking a particular activity, but wearable device 22 and/or patient device 24 may fail to determine that patient 12 is undertaking the particular activity.

Accordingly, in one or more examples, wearable device 22 and/or patient device 24 may"learn" to determine whether patient 12 is undertaking a particular activity. However, the computing resources of wearable device 22 and patient device 24 may be insufficient to performing the learning needed to determine whether patient 12 is undertaking a particular activity. It may be possible for the computing resources of wearable device 26 and patient device 24 to be sufficient to perform the learning, but for ease of description only, the following is described with respect to one or more processors 28 in cloud 26.

As illustrated in FIG. 1, system 10A includes cloud 26 that includes one or more processors 28. For example, cloud 26 includes a plurality of network devices (e.g., servers), and the plurality of devices each include one or more processors. One or more processors 28 may be processors of the plurality of network devices, and may be located within a single one of the network devices, or may be distributed across two or more of the network devices. Cloud 26 represents a cloud infrastructure that supports one or more processors 28 on which applications or operations requested by one or more users run. For example, cloud 26 provides cloud computing for using one or more processors 28, to store, manage, and process data on the network devices, rather than by personal device 24 or wearable device 22. One or more processors 28 may share data or resources for performing computations, and may be part of computing servers, web servers, database servers, and the like. One or more processors 28 may 28 may be in network devices (e.g., servers) within a datacenter or may be distributed across multiple datacenters. In some cases, the datacenters may be in different geographical locations.

One or more processors 28, as well as other processing circuitry described herein, can include any one or more microprocessors, digital signal processors (DSPs), application specific integrated circuits (ASICs), field programmable gate arrays (FPGAs), or any other equivalent integrated or discrete logic circuitry, as well as any combinations of such components. The functions attributed one or more processors 28, as well as other processing circuitry described herein, herein may be embodied as hardware, firmware, software or any combination thereof.

One or more processors 28 may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. One or more processors 28 may include arithmetic logic units (ALUs), elementary function units (EFUs), digital circuits, analog circuits, and/or programmable cores, formed from programmable circuits. In examples where the operations of one or more processors 28 are performed using software executed by the programmable circuits, memory (e.g., on the servers) accessible by one or more processors 28 may store the object code of the software that one or more processors 28 receive and execute.

In some examples, one or more processors 28 may be configured to determine patterns from gesture movements (e.g., as one or more movement characteristics determined by wearable device 22), and configured to determine a particular activity patient 12 is undertaking. One or more processors 28 may provide responsive real-time cloud services that can, on a responsive real-time basis, determine the activity patient 12 is undertaking, and in some examples, reduce alerts output by patient device 24 and/or provide recommended therapy (e.g., insulin dosage amount). Cloud 26 and patient device 24 may communicate via Wi-Fi or through a carrier network.

For example, as described above, in some examples, wearable device 22 and/or patient device 24 may be configured to determine that patient 12 is undertaking an activity. However, in some examples, patient device 24 may output information indicative of the movement characteristics of movement of the arm of patient 12 to cloud 26, and possibly with other contextual information like location, speed, and/or time of day (e.g., a patient may operate a vehicle at the same time during the work week going to and from work). One or more processors 28 of cloud 26 may then determine the activity patient 12 is undertaking. Insulin pump 14 may then deliver insulin based on the determined activity of patient 12 (e.g., reduce the amount of insulin to deliver while patient 12 is operating a vehicle to avoid the change of hypoglycemia and/or output fewer or no lower priority alerts while patient 12 is operating a vehicle). In addition, patient device 24 may be configured to output fewer, low priority alerts while patient 12 is operating a vehicle.

One example way in which one or more processors 28 may be configured to determine that patient 12 is undertaking an activity and determine therapy to deliver is described in U.S. patent Publication No. 2020/0135320 A1. In general, one or more processors 28 may 28 may first go through an initial "learning" phase, in which one or more processors 28 receive information to determine behavior patterns of patient 12. Some of this information may be provided by patient 12. For example, patient 12 may be prompted or may himself/herself enter information into patient device 24 indicating that patient 12 is undertaking a particular activity (e.g., driving), the length of the activity (e.g., how long is the trip, starting time, ending time, etc.), and other such information that one or more processors 28 can utilize to predict behavior of patient 12. After the initial learning phase, one or more processors 28 may still update the behavior patterns based on more recent received information, but require fewer to no information from patient 12.

In the initial learning phase, patient 12 may provide information about the dominant hand of patient 12 (e.g., right or left-handed and what hand is typically used to steer a vehicle) and where patient 12 wears wearable device 22 (e.g., around the wrist of right hand or left hand). Patient 12 may be instructed to wear wearable device 22 on the wrist of the hand patient 12 uses to drive most often. Patient 12 may also provide information about the orientation of wearable device 22 (e.g., face of wearable device 22 is on the top of the wrist or bottom of the wrist).

In the initial learning phase, patient 12 may enter, proactively or in response to prompt/query, information (e.g., through patient device 24) indicating that patient 12 is engaging in an activity (e.g., driving). During this time, wearable device 22 may continuously determine the one or more movement characteristics (e.g., gestures) and/or posture of patient 12, and output such information to patient device 24 that relays the information to one or more processors 28. One or more processors 28 may store information of the one or more movement characteristics of movement of the arm of patient 12 during the activity to later determine whether patient 12 is engaging in that activity (e.g., whether the received information of the manner and frequency of movement of the arm of patient 12 aligns with the stored information of the manner and frequency of movement of the arm of patient 12 when patient 12 was known to be engaging in that activity).

The above describes arm movement as a factor in determining whether patient 12 is engaging in an activity, such as operating a vehicle. However, there may be various other factors that can be used separately or in combination with arm movement to determine whether patient 12 is engaging in an activity. As one example, patient 12 may engage in the activity at regular time intervals or periods (e.g., before and after work). As another example, patient 12 may 12 may engage in the activity at certain locations. In the initial learning phase, when patient 12 enters that he or she is engaging in the activity (e.g., through patient device 24), patient device 24 may 24 may output information about the time of day and the location of patient 12. For example, patient device 24 may be equipped with a position-location sensor, such as global positioning system (GPS) unit, and patient device 24 may output location information and/or speed information determined by the GPS unit. There may be other ways to determine location and/or speed, such as based on Wi-Fi connection and/or access to 4G/5G LTE, or some other form of access, such as based on telecom database tracking device location of patient device 24. As another example, patient device 24 and/or processors 28 may further determine that patient 12 is operating a vehicle based on information received from a smartphone operating system (e.g., a vehicle detection by a smartphone operating system) and/or from a connection to a short-range communication system (e.g., Bluetooth connection to a stereo) of a vehicle. Other contextual information that patient device 24 and/or processors 28 may use to help determine that patient 12 is operating a vehicle may include a detection that patient device 24 (or another smartphone) is using a navigation application, detection of speeds, velocities, or vibrations that are indicative of vehicle travel, or other contextual clues. Time of day and location are another two examples of contextual information that can be used to determine whether patient 12 is engaging in the activity.

The contextual information for patient 12 may include conditional information. For example, patient 12 may drive every 8 hours, but the exact times of when patient 12 drives may be different. In general, any information that establishes a pattern of behavior may be utilized to determine whether patient 12 is engaging in a particular activity.

One or more processors 28 may utilize artificial intelligence, such as machine-learning or other data analytics techniques, based on the information determined by and/or collected by wearable device 22 and patient device 24 to determine whether patient 12 is engaging in the activity. As one example, during the initial learning phase, one or more processors 28 may utilize neural network techniques. For example, one or more processors 28 may receive training data from patient 12 that is used to train a classifier module executing on one or more processors 28. As described above, one or more processors 28 may receive the training data based on patient confirmation when patient device 24 and/or wearable device 22 determine, based on manner, position, and/or frequency of movement of the arm of patient 12, that patient 12 is engaging in the activity (e.g., one or more gestures that aligns with operating a vehicle). One or more processors 28 may generate and store a labeled data record that includes the features related to the movement, along with other contextual features, such as time of day or location. One or more processors 28 may train the classifier on a labeled dataset that includes multiple labeled data records, and one or more processors 28 may use the trained classifier model to more accurately detect the start of patient 12 operating a vehicle. Similarly, one or more processors 28 may train the classifier on a labeled dataset to more accurately detect the end of patient 12 operating a vehicle Other examples that may be used for neural networks include behavior patterns. For example, patient 12 may only operate a vehicle at a particular time of day and/or place. Although described with respect to driving, there may be various conditions that together indicate a pattern in behavior of patient 12 for different activities.

As another example, one or more processors 28 may utilize k-means clustering techniques to determine whether patient 12 is engaging in an activity. For example, during the initial learning phase one or more processors 28 may receive different types of contextual information and form clusters, where each cluster represents a behavior of patient 12 (e.g., eating, sleeping, walking, exercising, etc.). For example, patient 12 may enter information (e.g., into patient device 24) indicating that he or she is operating a vehicle. One or more processors 28 may utilize all the contextual information received when patient 12 is operating a vehicle to form a first cluster associated with operating vehicle. Patient 12 may enter information (e.g., into patient device 24) indicating that he or she is performing other tasks. One or more processors 28 may utilize all the contextual information received when patient 12 is performing other tasks to form a second cluster associated with those other tasks, and so on. Then, based on received contextual information, one or more processors 28 may determine which cluster aligns with the contextual information, and determine the activity patient 12 is undertaking. As described in more detail, the type of activity, and a prediction of when the activity will occur, may be utilized to determine when to delivery insulin therapy and/or manage alerts output by patient device 24.

There may be other examples of machine learning, and the example techniques are limited to any particular machine learning technique.

There may be various other ways in which one or more processors 28 may determine the activity patient 12 is undertaking. This disclosure provides some example techniques for determining the activity patient 12 is undertaking, but the example techniques should not be considered limiting.

In some examples, one or more processors 28 may be configured to determine an amount of insulin (e.g., therapy dosage of bolus insulin) to deliver to patient 12. As one example, memory accessible by one or more processors 28 may store patient parameters of patient 12 (e.g., weight, age, height, etc.). The memory may also store a look-up table that indicates an amount of bolus insulin that is to be delivered for different patient parameters and different types of foods. One or more processors 28 may access the memory and based on the type of food patient 12 is eating and patient parameters may determine the amount of bolus insulin that patient 12 is to receive.

In one example, the amount of insulin determined to deliver to patient 12, and the target blood glucose level for patient 12, may be referred to as a default therapy protocol. As was explained above, when patient device 24 and/or processors 28 determine that patient 12 is operating a vehicle, patient device 24 and/or processors 28 may configure insulin pump 14 to operate according to driving therapy protocol. The driving therapy protocol may raise the target glucose level and/or decrease the insulin dosage relative to the default therapy protocol.

As another example, one or more processors 28 may be configured to utilize a "digital twin" of patient 12 to determine an amount of bolus insulin patient 12 is to receive. A digital twin may be a digital replica or model of patient 12. The digital twin may be software executing on one or more processors 28. The digital twin may receive, as input, information about what patient 12 ate. Because the digital twin is a digital replica of patient 12, the output from the digital twin may be information about what the glucose level of patient 12 may be after eating, as well as a recommendation of how much bolus insulin to deliver to patient 12 to control the increase the glucose level.

For example, the digital twin may indicate what the correct dose should have been for a meal that patient 12 ate in the past. In one or more examples, patient 12 may enter information indicative of food patient 12 ate and one or more processors 28 may receive information about glucose levels. Utilizing information indicative of food that patient 12 ate and glucose levels, one or more processors 28 may utilize the digital twin to determine what the insulin dose should have been (e.g., based on how the digital twin models how the food will affect the patient's glucose level). Then, at a subsequent time when patient 12 is predicted to eat the same meal, one or more processors 28 may determine what the insulin dose should be based on insulin dose amount that the digital twin had previously determined.

Accordingly, in one or more examples, one or more processors 28 may utilize information about the movement characteristics of movement of arm, eating pace, quantity of food consumption, food content, etc., while also tracking other contextual information. Examples of the contextual information include location information, time of day, wake up time, amount of time since a last meal event, calendar event, information about person patient 12 may be meeting, etc. One or more processors 28 may identify patterns and correlations between all these various factors to determine an activity patient 12 undertaking, like eating, walking, sleeping, driving, etc.

After the initial learning phase, one or more processors 28 may automatically, and with minimal input from patient 12, determine that patient 12 is undertaking a particular activity (e.g., operating a vehicle). In one example of the disclosure, processors 28 may cause patient device 24 to output alerts according to a driving alert protocol based on the determination that the user is operating a vehicle. For example, when operating according to the driving alert protocol, patient device 24 may output or generate fewer alerts relative to a default alert protocol. In one example, when it is detected that a patient is operating a vehicle, patient device 24 may be configured to output or generate fewer alerts, so as to reduce distractions to the driver. Higher priority alerts (e.g., low blood glucose alert) may still be output, while lower priority alerts (e.g., low battery, meal reminders, etc.) may be disabled (e.g., not generated or output) and/or reduced in output frequency relative to a default alert protocol. A low blood glucose event detected by sensor 20 may be used to trigger the output a low blood glucose alert. Based on information received from sensor 20, one or more of patient device 24, wearable device 22, and/or insulin pump 14 may be configured to generate and/or output the low blood glucose alert if the blood glucose level is below some threshold (e.g., less than 70 mg/dl). In some examples, a low blood glucose event may be defined as a blood glucose level below a threshold for a specified period of time (e.g., 2 minutes).

In another example of the disclosure, processors 28 may cause insulin pump 14 to operate according to a driving therapy protocol based on the determination that the user is operating a vehicle. That is, processors 28 may cause insulin pump 14 to raise the target blood glucose level and/or reduce a dosage of insulin relative to a default therapy protocol based on determining that patient 12 is operating a vehicle. One or more processors 28 may output the recommendation of the amount of bolus insulin to deliver to patient device 24. Patient device 24, may then in turn, control insulin pump 14 to deliver the determined amount of insulin. As one example, patient device 24 may output to insulin pump 14 the amount of bolus insulin to deliver with or without user confirmation. As another example, patient device 24 may output a target glucose level, and insulin pump 14 may deliver the insulin to achieve the target glucose level. In some examples, it may be possible for one or more processors 28 to output to patient device 24 information indicative of the target glucose level, and patient device 24 may output that information to insulin pump 16. All of these examples may be considered as examples of one or more processors 28 determining an amount of insulin to deliver to patient 12.

The above describes example ways in which to determine if patient 12 is undertaking an activity, determining an alert protocol, determining an amount of insulin to deliver, and causing the amount of insulin to be delivered. The example techniques may require little to no intervention from patient 12. In this manner, there is an increase in likelihood that patient 12 will receive the correct amount of dosage of insulin at the right time, and decrease in likelihood of human error causing issues (e.g., patient 12 forgetting to log meals, forgetting to take insulin, or taking insulin but forgetting to have taken insulin). The techniques of this disclosure may also reduce driver distractions when it is detected that patient 12 is operating a vehicle and may also reduce the likelihood of a hypoglycemic even when patient 12 is operating a vehicle. The techniques of this disclosure may further extend the battery life of insulin pump 14 and/or patient device 24 by reducing the number of alerts that are generated/output.

In summary, this disclosure describes systems and techniques for outputting patient alerts related to diabetes therapy. In one example, the system may include a patient device configured to output one or more alerts, the one or more alerts including alerts related to the diabetes therapy. In one example, the patient device of this disclosure is patient device 24 described above. In other examples, other devices may be considered to be patient devices configured to output alerts. For example, a device configured to output alerts may include wearable device 22 and/or insulin pump 14.

The system may further include one or more processors configured to determine whether patient 12 is operating a vehicle and update one or more of an alert protocol or a therapy protocol. An alert protocol may specify what type of alerts (e.g., low priority alerts or high priority alerts) may be output and at what output frequency such alerts may be output. The therapy protocol may instruct insulin pump 14 how to administer therapy to patient 12, where the therapy may be administered according to a target blood glucose level and/or a specific insulin dosage. In this context, the one or more processors that are configured to determine whether patient 12 is operating a vehicle and update one or more of an alert protocol or a therapy protocol are not limited to processors 28 shown in FIG. 1. Any device that includes one or more processors may be configured to make the determination of whether patient 12 is driving and update alert and therapy protocols, including patient device 24, cloud 26, wearable device 22, insulin pump, or another device.

In one example, processors 28 may be configured to detect a gesture of patient 12, and determine, based at least in part on the gesture, that patient 12 is operating a vehicle. As described above, in some examples, processors 28 may be configured to determine that patient 12 is operating a vehicle based on multiple gestures over time, and using one or more static postures of patient 12. In other examples, processors 28 may use additional information to verify that patient 12 is operating a vehicle. For example, the system 10A may include a position-location sensor (e.g., a GPS sensor) that is configured to determine a speed of patient 12. Processors 28 may use the speed of patient 12 along with the detected gesture to determine that patient 12 is operating the vehicle. Using both speed as well as the gesture of patient 12 to determine that patient 12 is operating the vehicle is beneficial, because using speed alone may cause a determination that patient 12 is operating a vehicle in situations where patient 12 is just a passenger. Using gestures to determine that patient 12 is operating the vehicle helps better ensure that therapy and alerts are altered in situations where it is beneficial to do so (i.e., while patient 12 is driving). As another example, patient device 24 and/or processors 28 may further determine that patient 12 is operating a vehicle based on information received from a smartphone operating system (e.g., a vehicle detection by a smartphone operating system) and/or from a connection to a short-range communication system (e.g., Bluetooth) of a vehicle.

Processors 28 may be further configured to instruct patient device 24 to output one or more alerts according to a driving alert protocol based on the determination that patient 12 is operating the vehicle. As described above, the driving alert protocol reduces an output frequency of a portion of the one or more alerts relative to a default alert protocol. When operating according the driving alert protocol, patient device 24 may output higher priority alerts (e.g., low blood glucose alert), but may disable and/or reduce the output frequency of lower priority alerts (e.g., low battery, meal reminders, etc.) relative to a default alert protocol.

Accordingly, in one example of the disclosure, patient device 24 is configured to reduce the output frequency of the low priority alerts when operating according to the driving alert protocol. In another example of the disclosure, patient device 24 is configured to disable the low priority alerts when operating according to the driving alert protocol. In still other examples of the disclosure, patient device 24 is configured to output high priority alerts when operating according to the driving alert protocol. In some examples, patient device 24 is a smartphone, and such smartphone may disable some alerts and/or notifications automatically if the smartphone is detected as being in a vehicle (e.g., the smartphone may be in a "do not disturb" mode). In accordance with the techniques of this disclosure, patient device 24 may be configured to override any disablement of higher priority diabetes related alerts (e.g., a low blood sugar event) when operating according to the driving alert protocol, even if patient device 24 is in a "do not disturb" mode.

In a further example of the disclosure, processors 28 may be configured to continually and/or periodically analyze gestures of patient 12 to determine if the patient has stopped operating the vehicle. For example, processors 28 may be configured to detect an updated gesture of patient 12, and determine, based at least in part on the updated gesture, that patient 12 is no longer operating the vehicle. In this circumstance, processors 28 may instruct patient device 24 to output the one or more alerts according to the default alert protocol based on the determination that patient 12 is no longer operating the vehicle.

In each of the examples above for determining whether patient 12 is operating the vehicle or not operating the vehicle, processors 28 may be configured to switch the operation of patient device 24 onto and off of the driving alert protocol after a certain buffer period. That is, in some examples, the alert protocol is not switched immediately on detection of operating a vehicle or not operation vehicle, but rather after a certain prescribed time of vehicle operation detection. For example, processors 28 may be configured to instruct patient device 24 to operate according to the driving alert protocol after vehicle operation has been detected for a period of time (e.g., 2 minutes). Likewise, processors 28 may be configured to instruct patient device 24 to operate according to the default alert protocol after the cessation of vehicle operation has been detected for the same of different period of time (e.g., 2-5 minutes). Of course, any buffer period of time may be used.

In other example of the disclosure, processors 28 are configured to determine a driving therapy protocol based on the determination that patient 12 is operating the vehicle. As described above, the driving therapy protocol includes one or more of reducing a dosage of insulin or raising a target blood glucose level. In one example, processors 28 are further configured to communicate the driving therapy protocol to patient device 24. In another example, processors 28 and/or patient device 24 are configured to communicate the driving therapy protocol to insulin pump 14. Insulin pump 14 is then configured to operate according to the driving therapy protocol.

Figure 2:
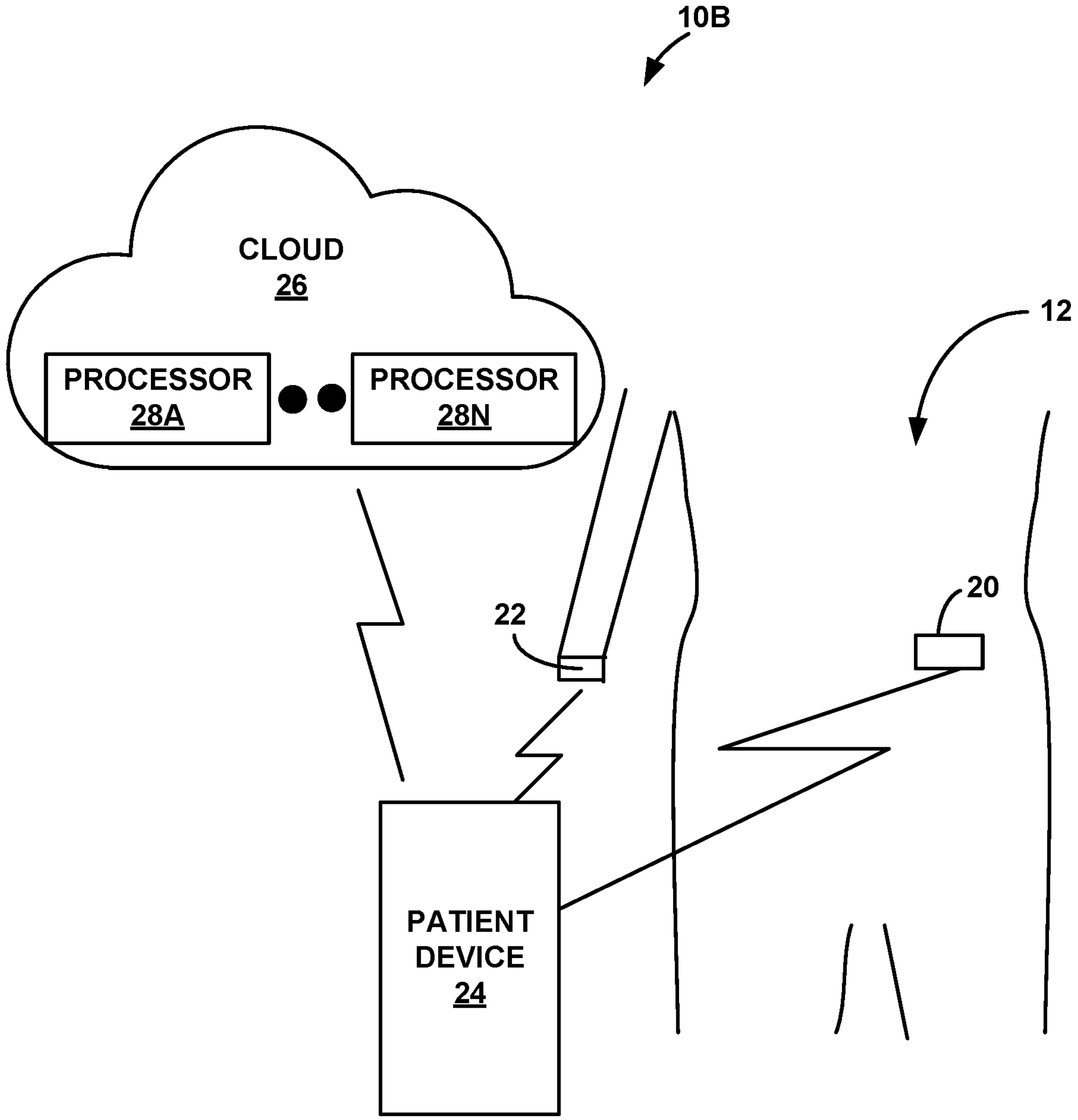
FIG. 2 is a block diagram illustrating another example system for delivering or guiding therapy dosage, in accordance with one or more examples described in this disclosure.

FIG. 2 is a block diagram illustrating another example system for delivering or guiding therapy dosage, in accordance with one or more examples described in this disclosure. FIG. 2 illustrates system 10B that is similar to system 10A of FIG. 1. However, in system 10B, patient 12 may not have insulin pump 14. Rather, patient 12 may utilize a manual injection device (e.g., an insulin pen or a syringe) to deliver insulin. For example, rather than insulin pump 14 automatically delivering insulin, patient 12 (or possible a caretaker of patient 12) may fill a syringe with insulin or set the dosage amount in an insulin pen and inject himself or herself.

In this example, processors 28 are configured to detect vehicle operation and set an alert protocol of patient device 24 in the same manner as described above for FIG. 1. However, rather than setting a driving therapy protocol for insulin pump 14, processors 28 may be configured to send an alert or notification to patient 12 to not manually inject insulin or to reduce a dosage amount in the case that vehicle operation is detected.

Figure 3:
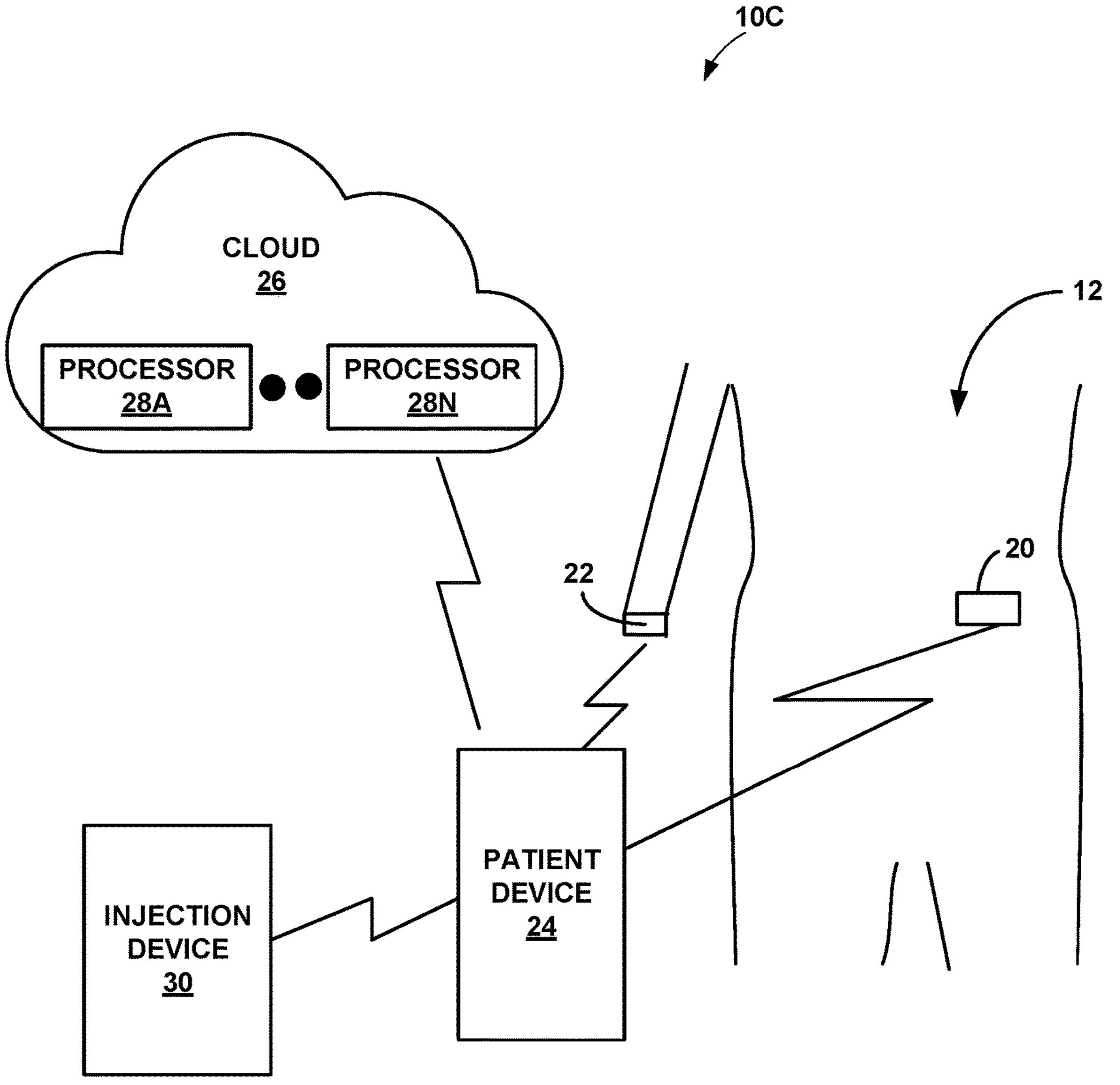
FIG. 3 is a block diagram illustrating another example system for delivering or guiding therapy dosage, in accordance with one or more examples described in this disclosure.

FIG. 3 is a block diagram illustrating another example system for delivering or guiding therapy dosage, in accordance with one or more examples described in this disclosure. FIG. 3 illustrates system 10C that is similar to system 10A of FIG. 1 and system 10B of FIG. 2. In system 10C, patient 12 may not have insulin pump 14. Rather, patient 12 may utilize injection device 30 to deliver insulin. For example, rather than insulin pump 14 automatically delivering insulin, patient 12 (or possible a caretaker of patient 12) may utilize injection device 30 to inject himself or herself.

Injection device 30 may be different than a syringe because injection device 30 may be a device that can communicate with patient device 24 and/or other devices in system 10C. Also, injection device 30 may include a reservoir, and based on information indicative of how much therapy dosage to deliver may be able to dose out that much insulin for delivery. For example, injection device 30 may automatically set the amount of insulin based on the information received from patient device 24. In some examples, injection device 30 may be similar to insulin pump 14, but not worn by patient 12. One example of injection device 30 is an insulin pen, sometimes also called a smart insulin pen. Another example of injection device 30 may be an insulin pen with a smart cap, where the smart cap can be used to set particular doses of insulin.

In this example, processors 28 are configured to detect vehicle operation and set an alert protocol of patient device 24 in the same manner as described above for FIG. 1. However, rather than setting a driving therapy protocol for insulin pump 14, processors 28 may be configured to send an alert or notification to patient 12 to not manually inject insulin or to reduce a dosage amount in the case that vehicle operation is detected.

The above examples described insulin pump 14, a syringe, and injection device 30 as example ways in which to deliver insulin. In this disclosure, the term "insulin delivery device" may generally refer to any device used to deliver insulin. Examples of insulin delivery device include insulin pump 14, a syringe, and injection device 30. As described, the syringe may be a device used to inject insulin but is not necessarily capable of communicating or dosing a particular amount of insulin. Injection device 30, however, may be a device used to inject insulin that may be capable of communicating with other devices (e.g., via Bluetooth, BLE, and/or Wi-Fi) or may be capable of dosing a particular amount of insulin. Injection device 30 may be powered (e.g., battery powered) device, and the syringe may be device that requires no power.

Figure 4:
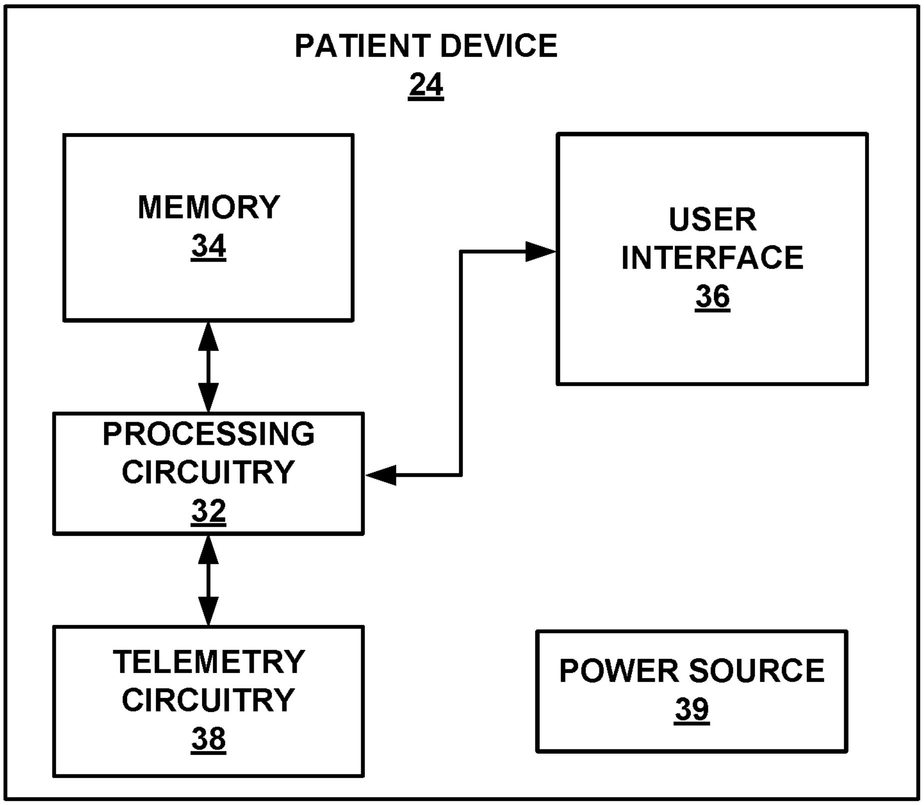
FIG. 4 is a block diagram illustrating an example of a patient device, in accordance with one or more examples described in this disclosure.

FIG. 4 is a block diagram illustrating an example of a patient device, in accordance with one or more examples described in this disclosure. While patient device 24 may generally be described as a hand-held computing device, patient device 24 may be a notebook computer, a cell phone, or a workstation, for example. In some examples, patient device 24 may be a mobile device, such as a smartphone or a tablet computer. In such examples, patient device 24 may 24 may execute an application that allows patient device 24 to perform example techniques described in this disclosure. In some examples, patient device 24 may be specialized controller for communicating with insulin pump 14.

Although the examples are described with one patient device 24, in some examples, patient device 24 may be a combination of different devices (e.g., mobile device and a controller). For instance, the mobile device may provide access to one or more processors 28 of cloud 26 through Wi-Fi or carrier network and the controller may provide access to insulin pump 14. In such examples, the mobile device and the controller may communicate with one another through Bluetooth or BLE. Various combinations of a mobile device and a controller together forming patient device 24 are possible and the example techniques should not be considered limited to any one particular configuration.

As illustrated in FIG. 4, patient device 24 may include a processing circuitry 32, memory 34, user interface 36, telemetry circuitry 38, and power source 39. Memory 34 may store program instructions that, when executed by processing circuitry 32, cause processing circuitry 32 to provide the functionality ascribed to patient device 24 throughout this disclosure.

In some examples, memory 34 of patient device 24 may store a plurality of parameters, such as amounts of insulin to deliver, target glucose level, time of delivery etc. Processing circuitry 32 (e.g., through telemetry circuitry 38) may output the parameters stored in memory 34 to insulin pump 14 or injection device 30 for delivery of insulin to patient 12. In some examples, processing circuitry 32 may execute a notification application, stored in memory 34, that outputs notifications to patient 12, such as notification and/or alerts to take insulin, amount of insulin, and time to take the insulin, via user interface 36.

Furthermore, as described above processing circuitry 32 of patient device 24 may be configured to reduce the output frequency of the low priority alerts when operating according to the driving alert protocol. In another example of the disclosure, processing circuitry 32 of patient device 24 is configured to disable the low priority alerts when operating according to the driving alert protocol. In still other examples of the disclosure, processing circuitry 32 of patient device 24 is configured to output high priority alerts when operating according to the driving alert protocol. In some examples, patient device 24 is a smartphone, and such smartphone may disable some alerts and/or notifications automatically if the smartphone is detected as being in a vehicle. In accordance with the techniques of this disclosure, processing circuitry 32 of patient device 24 may be configured to override any disablement of higher priority diabetes related alerts (e.g., a low blood sugar event) when operating according to the driving alert protocol.

Memory 34 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 32 can take the form one or more microprocessors, DSPs, ASICs, FPGAs, programmable logic circuitry, or the like, and the functions attributed to processing circuitry 32 herein may be embodied as hardware, firmware, software or any combination thereof.

User interface 36 may include a button or keypad, lights, a speaker for voice commands, and a display, such as a liquid crystal (LCD). In some examples the display may be a touchscreen. As discussed in this disclosure, processing circuitry 32 may present and receive information relating to therapy via user interface 36. For example, processing circuitry 32 may receive patient input via user interface 36. The patient input may be entered, for example, by pressing a button on a keypad, entering text, or selecting an icon from a touchscreen. The patient input may be information indicative of food that patient 12 eats, such as for the initial learning phase, whether patient 12 took the insulin (e.g., through the syringe or injection device 30), and other such information.

Telemetry circuitry 38 includes any suitable hardware, firmware, software or any combination thereof for communicating with another device, such as cloud 26, insulin pump 16 or injection device 30, as applicable, wearable device 22, and sensor 20. Telemetry circuitry 38 may receive communication with the aid of an antenna, which may be internal and/or external to patient device 24. Telemetry circuitry 38 may be configured to communicate with another computing device via wireless communication techniques, or direct communication through a wired connection. Examples of local wireless communication techniques that may be employed to facilitate communication between patient device 24 and another computing device include RF communication according to IEEE 802.11, Bluetooth, or BLE specification sets, infrared communication, e.g., according to an IrDA standard, or other standard or proprietary telemetry protocols. Telemetry circuitry 38 may also provide connection with carrier network for access to cloud 26. In this manner, other devices may be capable of communicating with patient device 24.

Power source 39 delivers operating power to the components of patient device 24. In some examples, power source 39 may include a battery, such as a rechargeable or non-rechargeable battery. A non-rechargeable battery may be selected to last for several years, while a rechargeable battery may be inductively charged from an external device, e.g., on a daily or weekly basis. Recharging of a rechargeable battery may be accomplished by using an alternating current (AC) outlet or through proximal inductive interaction between an external charger and an inductive charging coil within patient device 24

Figure 5:
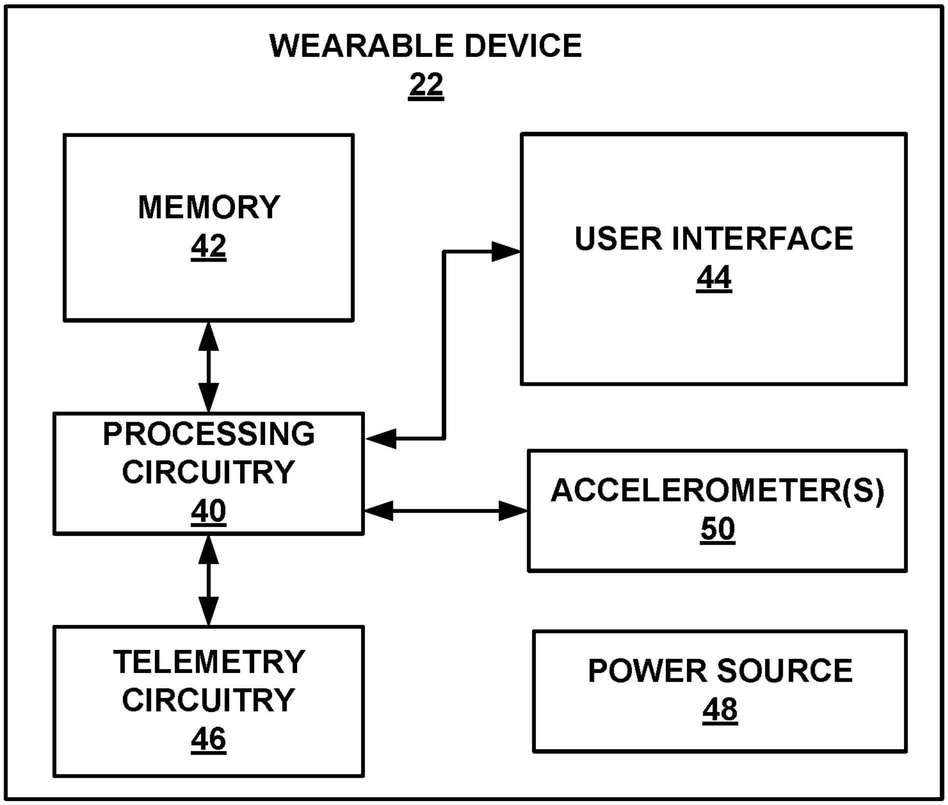
FIG. 5 is a block diagram illustrating an example of a wearable device, in accordance with one or more examples described in this disclosure.

FIG. 5 is a block diagram illustrating an example of a wearable device, in accordance with one or more examples described in this disclosure. As illustrated, wearable device 22 includes processing circuitry 40, memory 42, user interface 44, telemetry circuitry 46, power source 48, and inertial measurement units 50. Processing circuitry 40, memory 42, user interface 44, telemetry circuitry 46, and power source 48 may be similar to processing circuitry 32, memory 34, user interface 36, telemetry circuitry 38, and power source 39 of FIG. 4, respectively.

Inertial measurement units 50 may include gyroscopes and/or various components to determine a pitch-roll-yaw, and x-y-z coordinate of wearable device 22. In some examples, inertial measurement units 50 may be considered as a six-axis inertial measurement unit. For example, inertial measurement units 50 may couple a 3-axis accelerometer with a 3-axis gyroscope. The accelerometer may measure linear acceleration, while the gyroscope may measure rotational motion. Processing circuitry 40 may be configured to determine one or more movement characteristics based on values from inertial measurement units 50. For example, processing circuitry 40 may determine based on values from inertial measurement units 50 if patient 12 is moving his or her arm upwards, downwards, leftwards, rightwards, forwards, backwards, or some combination, including values related to frequency, amplitude, trajectory, position, velocity, acceleration, and/or pattern of movement. Processing circuitry 40 may determine based on values from one or more accelerometers 50 orientation of the arm of patient 12, such as whether the back of the hand or the front of the hand is facing patient 12, or if a side of the hand is facing patient 12, such that the thumb is facing patient 12 and the side of the index finger is visible.

As one example, when patient 12 is holding a steering wheel, patient 12 may orient his or her wrist in a particular manner, which may be different than if patient 12 is holding a different object. Other gestures that may be indicative of driving may include gestures related to interacting with vehicle controls, including forearm rotation (e.g., both pronation and supination for light steering of the wheel), hand-over-hand motions (e.g., for larger turns of the wheel), grasping (e.g., to hold the steering wheel), up and down motions of the left hand (e.g., to activate turn signals), and back-and-forth motions of the right hand (e.g., shifting the transmission). Of course, wearable device 22 may be configured to detect other gestures that are indicative of operating a vehicle. There may be a difference in the movement characteristics, and different output values from inertial measurement units 50. However, for all of the movement characteristics, one or more processors (including processing circuitry 40 in some examples) may be configured to determine that patient 12 is driving. In addition, as mentioned above, wearable device 22 may also detect certain static postures that are indicative of driving. Such static postures may include both hands held out away from the chest (e.g., when both hands are on the steering wheel) and/or one handheld out away from the chest with another hand in the patient's lap (e.g., one hand on the steering wheel).

Inertial measurement units 50 may output such information (e.g., pitch-roll-yaw and x-y-z coordinates) of the arm of patient 12 to processing circuitry 40. Telemetry circuitry 46 may then output the information from processing circuitry 40 to patient device 24. Patient device 24 may forward the information to one or more processors 28 that can use the information to determine if patient 12 is operating a vehicle.

Figure 6:
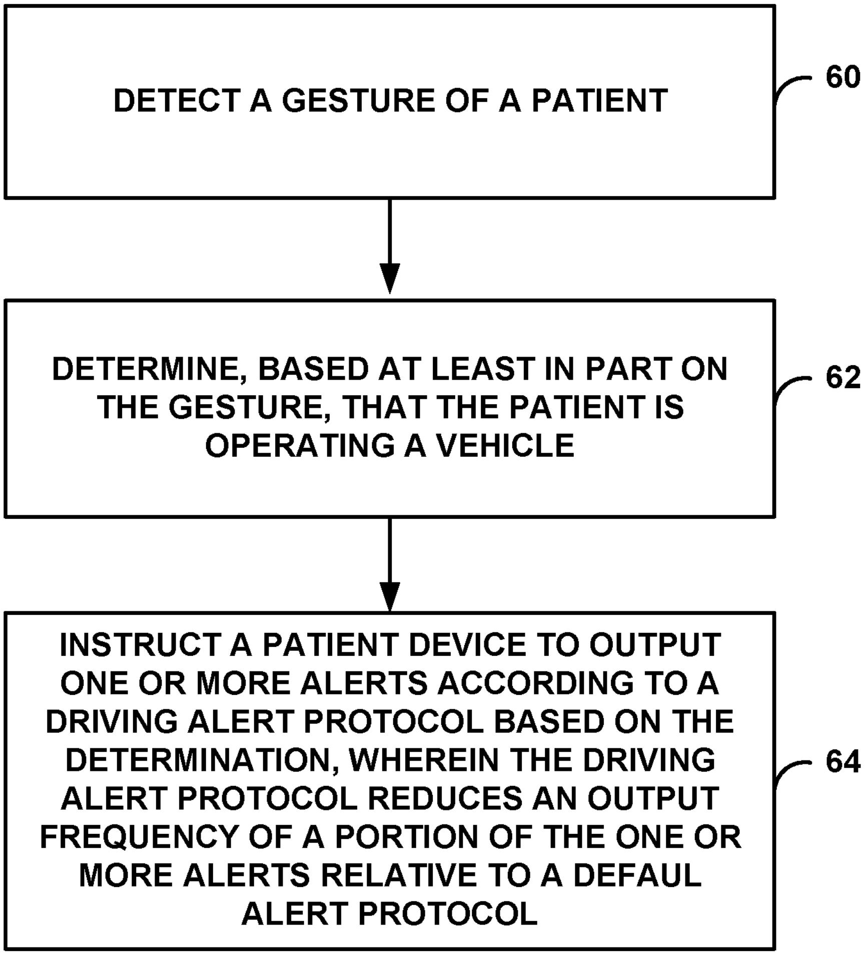
FIG. 6 is a flowchart illustrating an example technique of the disclosure for adjusting patient alerts.

FIG. 6 is a flowchart illustrating an example technique of the disclosure for adjusting patient alerts. The techniques of FIG. 6 may be performed by one or more devices that include one or more processors, including patient device 24, insulin pump 14, wearable device 22, and/or processors 28 of cloud 26 (see FIG. 1). In one example of the disclosure, one or more processors may detect a gesture of a patient (60). As described above, the one or more processors may detect the gesture from one data produced by one or more sensors of wearable device 22. The one or more processors may further be configured to determine, based at least in part on the gesture, that the patient is operating a vehicle (62). The one or more processors may then instruct a patient device (e.g., patient device 24 of FIG. 1) to output one or more alerts according to a driving alert protocol based on the determination (64). In one example, the driving alert protocol reduces an output frequency of a portion of the one or more alerts (e.g., low priority alerts) relative to a default alert protocol.

Example techniques of this disclosure are described with relation to patient device 24 outputting one or more alerts and adjusting how such alerts are output when it is detected that patient 12 is driving a vehicle. However, the techniques of this disclosure apply equally to any alerts output or generated by any of insulin pump 14, patient device 24, and/or wearable device 22. For example, insulin pump 14 may generate alerts to be output by patient device 24 and/or wearable device 22. The techniques of this disclosure may cause insulin pump to refrain from generating and/or transmitting lower priority alerts in the situation where it is detected that patient 12 is driving.

Figure 7:
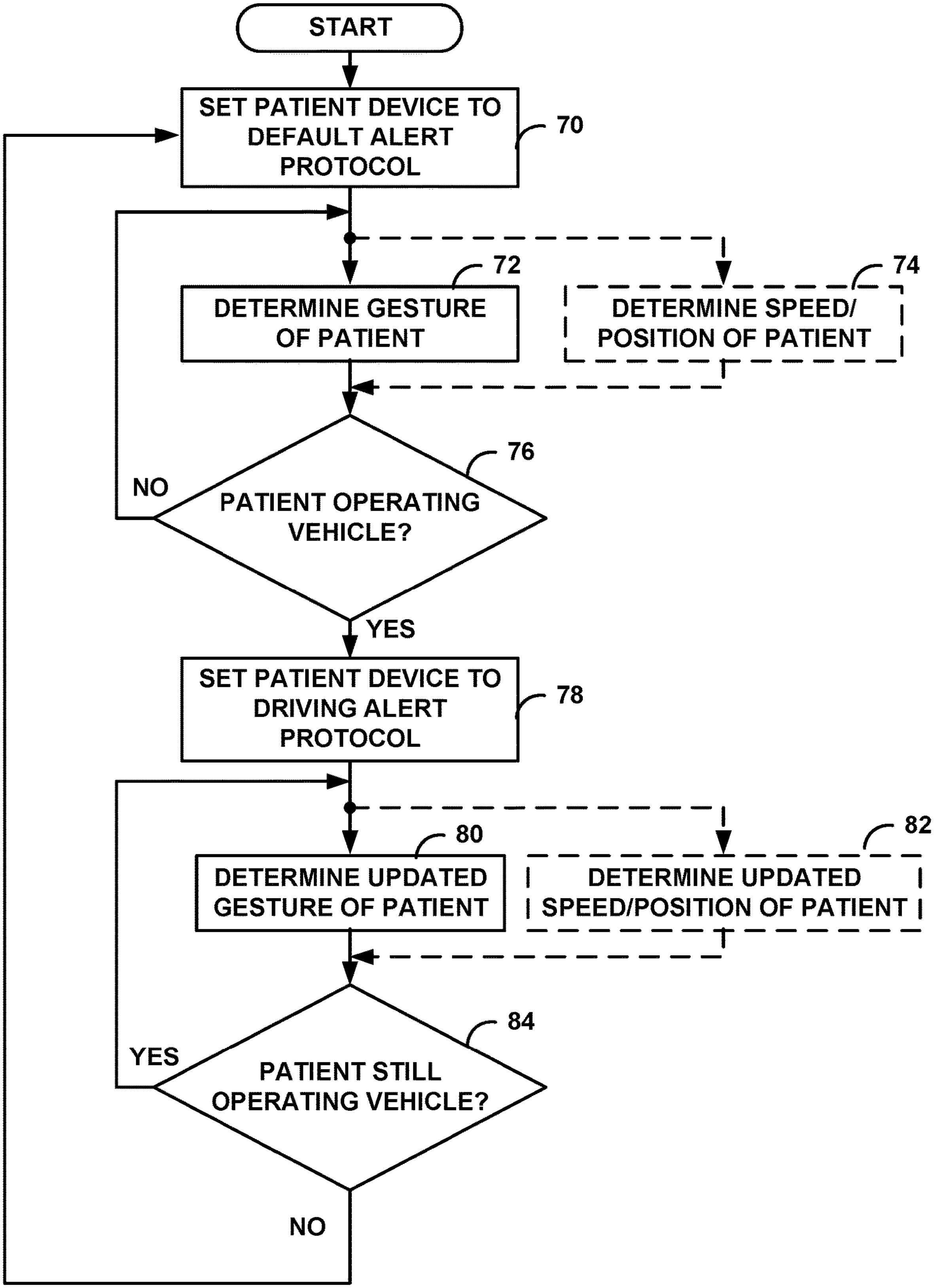
FIG. 7 is a flowchart illustrating another example technique of the disclosure for adjusting patient alerts.

FIG. 7 is a flowchart illustrating another example technique of the disclosure for adjusting patient alerts. The techniques of FIG. 7 may be performed by one or more devices that include one or more processors, including patient device 24, insulin pump 14, wearable device 22, and/or processors 28 of cloud 26 (see FIG. 1). In one example of the disclosure, one or more processors may set a patient device (e.g., patient device 24) to a default alert protocol (70). The one or more processors may then determine a gesture of a patient (72), e.g. using any of the gesture detection techniques described above. Optionally, the one or more processors may be further configured to determine a speed and/or position of a patient, e.g., using a position-location sensor as described above (74).

The one or processors may then determine if the patient is operating a vehicle based on the determined gesture or the determined gesture and speed/position (76). As another example, the one or more processors may further determine (e.g., in addition to the gesture-based detection) that patient 12 is operating a vehicle based on information received from a smartphone operating system (e.g., a vehicle detection by a smartphone operating system) and/or from a connection to a short-range communication system (e.g., Bluetooth) of a vehicle. The one or more processors may use the gesture detection to discern if patient 12 is driving the vehicle as opposed to just a passenger. If no, the one or more processors continue to determine the gesture (72) or gesture and speed position (72 and 74) of the patient. If the one or more processors determine that the patient is operating the vehicle, the one or more processors may set a patient device (e.g., patient device 24) to a driving alert protocol (78), as described above.

The one or more processors may then determine an updated gesture of the patient (80). Optionally, the one or more processors may be further configured to determine an updated speed and/or position of a patient (82). The one or processors may then determine if the patient is still operating a vehicle based on the updated gesture or the updated gesture and speed/position (84). Again, in other examples, the one or more processors may further determine (e.g., in addition to the gesture-based detection) that patient 12 is operating a vehicle based on information received from a smartphone operating system (e.g., a vehicle detection by a smartphone operating system) and/or from a connection to a short-range communication system (e.g., Bluetooth) of a vehicle. If no, the one or more processors continue to determine the updated gesture (80) or updated gesture and speed position (80 and 82) of the patient. If the one or more processors determine that the patient is not still operating the vehicle, the one or more processors set the patient device to the default alert protocol and continue the process (70).

Figure 8:
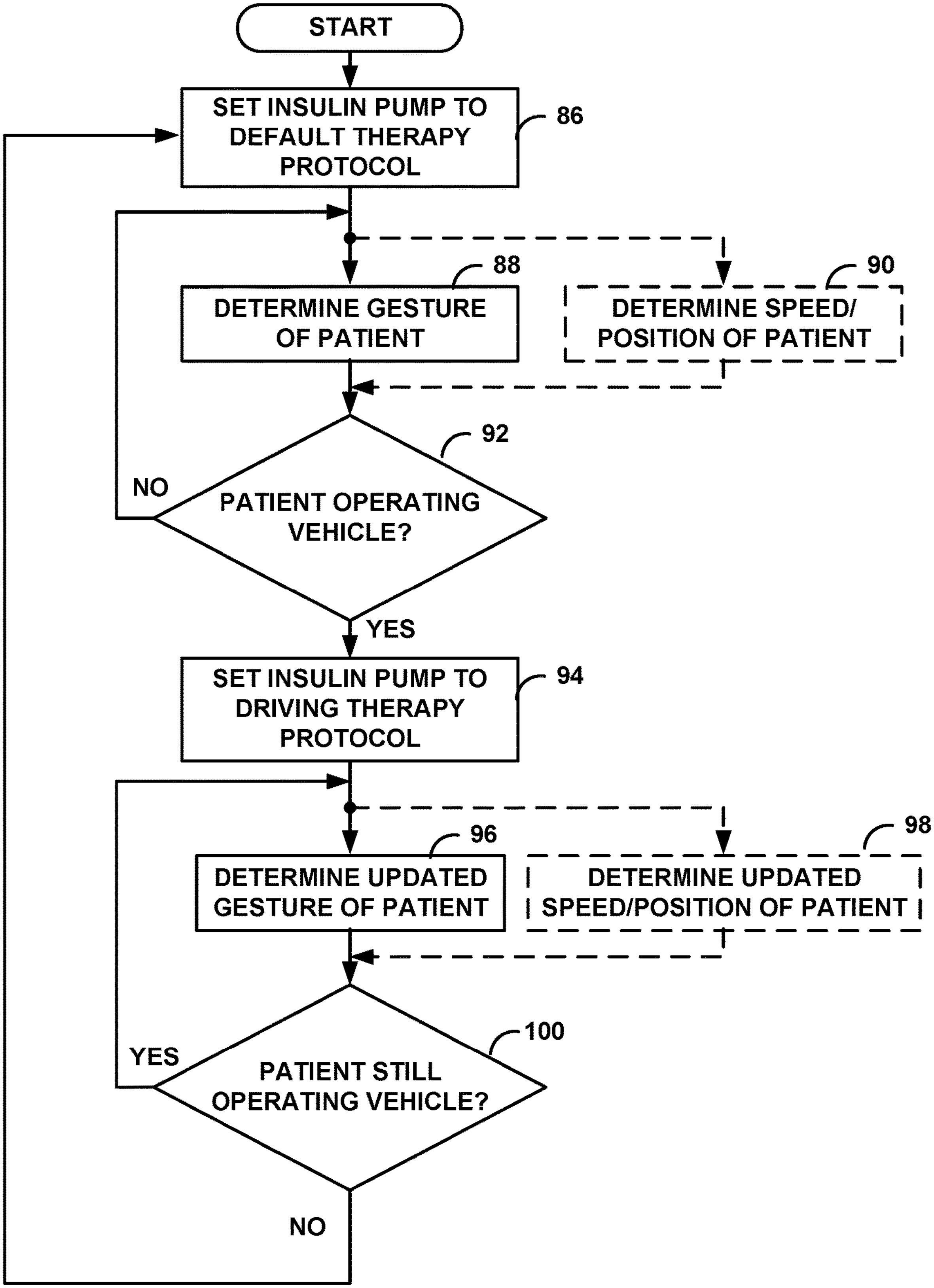
FIG. 8 is a flowchart illustrating an example technique of the disclosure for adjusting therapy.

FIG. 8 is a flowchart illustrating an example technique of the disclosure for adjusting therapy. The techniques of FIG. 8 may be performed by one or more devices that include one or more processors, including patient device 24, insulin pump 14, wearable device 22, and/or processors 28 of cloud 26 (see FIG. 1). In one example of the disclosure, one or more processors may set an insulin pump (e.g., pump 14) to a default therapy protocol (86). The one or more processors may then determine a gesture of a patient (88), e.g. using any of the gesture detection techniques described above. Optionally, the one or more processors may be further configured to determine a speed and/or position of a patient, e.g., using a position-location sensor (90).

The one or processors may then determine if the patient is operating a vehicle based on the determined gesture or the determined gesture and speed/position (92). As another example, the one or more processors may further determine (e.g., in addition to the gesture-based detection) that patient 12 is operating a vehicle based on information received from a smartphone operating system (e.g., a vehicle detection by a smartphone operating system) and/or from a connection to a short-range communication system (e.g., Bluetooth) of a vehicle. The one or more processors may use the gesture detection to discern if patient 12 is driving the vehicle as opposed to just a passenger. If no, the one or more processors continue to determine the gesture (88) or gesture and speed position (88 and 90) of the patient. If the one or more processors determine that the patient is operating the vehicle, the one or more processors may set an insulin pump (e.g., insulin pump) to a driving therapy protocol (94), as described above.

The one or more processors may then determine an updated gesture of the patient (96). Optionally, the one or more processors may be further configured to determine an updated speed and/or position of a patient (98). The one or processors may then determine if the patient is still operating a vehicle based on the updated gesture or the updated gesture and speed/position (100). Again, in other examples, the one or more processors may further determine (e.g., in addition to the gesture-based detection) that patient 12 is operating a vehicle based on information received from a smartphone operating system (e.g., a vehicle detection by a smartphone operating system) and/or from a connection to a short-range communication system (e.g., Bluetooth) of a vehicle. If no, the one or more processors continue to determine the updated gesture (96) or updated gesture and speed position (96 and 98) of the patient. If the one or more processors determine that the patient is not still operating the vehicle, the one or more processors set the insulin pump to the default therapy protocol and continue the process (86).

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors 28 of cloud 26, one or more processors of patient device 24, one or more processors of wearable device 22, one or more processors of insulin pump 14, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. An insulin pump for delivery of diabetes therapy, the insulin pump comprising:
- one or more processors configured to:
  - determine, based on a connection to a short-range communication system of a vehicle, that a patient is in the vehicle;
  - determine, based at least in part on movement data, that the patient is operating the vehicle;
  - determine that more than a predetermined buffer period of time has elapsed since the patient began operating the vehicle;
  - in response to determining that the patient is operating the vehicle and more than the predetermined buffer period of time has elapsed:
    - determine a driving therapy protocol;
    - automatically implement, without patient confirmation, the driving therapy protocol to deliver insulin to maintain a glucose level of the patient above a hypoglycemia threshold; and
    - inhibit generation of low priority alerts while continuing generation of high priority alerts.

2. The insulin pump of claim 1, wherein the one or more processors are further configured to:
- detect a gesture of the patient;
- determine, based at least in part on the gesture, that the patient is no longer operating the vehicle; and
- resume a default therapy protocol based on the determination that the patient is no longer operating the vehicle.

3. The insulin pump of claim 1, wherein the driving therapy protocol comprises reducing a dosage of insulin relative to a default dosage.

4. The insulin pump of claim 1, wherein the driving therapy protocol comprises increasing a target glucose level relative to a default target glucose level.

5. The insulin pump of claim 1, wherein the movement data comprises gesture data that is obtained by a wearable device worn by the patient.

6. The insulin pump of claim 5, wherein the gesture data is received by the one or more processors of the insulin pump via an intermediary patient device communicatively coupling the wearable device and the insulin pump.

7. The insulin pump of claim 1, wherein the driving therapy protocol is one that reduces a likelihood of hypoglycemia relative to a default therapy protocol.

8. The insulin pump of claim 1, wherein inhibiting low priority alerts comprises inhibiting alerts related to one or more of: reminders to take medication, reminders to eat, a low battery of the insulin pump, or an alert to change a glucose sensor communicatively coupled to the insulin pump.

9. The insulin pump of claim 1, wherein the insulin pump is coupled to the short-range communication system of the vehicle.

10. The insulin pump of claim 1, wherein the driving therapy protocol causes the diabetes therapy to be managed differently when the patient is operating the vehicle relative to when the patient is a passenger in the vehicle.

11. A method for delivery of diabetes therapy, the method comprising:
- determining, by one or more processors of an insulin pump and based on a connection to a short-range communication system of a vehicle, that a patient is in the vehicle;
- determining, based at least in part on movement data, that the patient is operating the vehicle;
- determining that more than a predetermined buffer period of time has elapsed since the patient began operating the vehicle;
- in response to determining that the patient is operating the vehicle and more than the predetermined buffer period of time has elapsed:
- determining, using the one or more processors of the insulin pump, a driving therapy protocol based on the determination that the patient is operating the vehicle;
- automatically implementing, without patient confirmation, the driving therapy protocol to deliver insulin to maintain a glucose level of the patient above a hypoglycemia threshold; and inhibiting, by the one or more processors of the insulin pump, generation of low priority alerts while continuing generation of high priority alerts.

12. The method of claim 11, further comprising:

detecting a gesture of the patient;

determining, based at least in part on the gesture, that the patient is no longer operating the vehicle; and resuming a default therapy protocol based on the determination that the patient is no longer operating the vehicle.

13. The method of claim 11, wherein the driving therapy protocol comprises reducing a dosage of insulin relative to a default dosage and/or increasing a target glucose level relative to a default target glucose level.

14. The method of claim 11, wherein the movement data comprises gesture data that is obtained by a wearable device worn by the patient.

15. The method of claim 14, wherein the gesture data is received by the one or more processors of the insulin pump via an intermediary patient device communicatively coupling the wearable device and the insulin pump.

16. The method of claim 11, wherein continuing the generation of the high priority alerts comprises overriding a setting that inhibits presentation of all alerts.

17. The method of claim 11, wherein the insulin pump is coupled to the short-range communication system of the vehicle.

18. A method for delivery of diabetes therapy, the method comprising:

determining, by one or more processors of an insulin pump based at least in part on gesture data received from a wearable device worn by a patient, that the patient is operating a vehicle;

determining that more than a predetermined buffer period of time has elapsed since the patient began operating the vehicle:

determining, using the one or more processors of the insulin pump, a driving therapy protocol based on the determination that the patient is operating the vehicle and that more than the predetermined buffer period of time has elapsed; and automatically implementing, without patient confirmation, the driving therapy protocol to deliver, by the insulin pump, insulin to maintain a glucose level of the patient above a hypoglycemia threshold while concurrently modifying, by the one or more processors of the insulin pump, presentation of alerts on the wearable device by inhibiting low priority alerts not related to the glucose level of the patient and presenting high priority alerts related to the glucose level of the patient on the wearable device.

19. The method of claim 18, wherein modifying, by the one or more processors of the insulin pump, presentation of alerts on the wearable device by inhibiting the low priority alerts comprises pausing transmission of the low priority alerts from the insulin pump to the wearable device.

* * * * *